(12) United States Patent
Kostrzewski

(10) Patent No.: US 8,074,859 B2
(45) Date of Patent: Dec. 13, 2011

(54) SURGICAL INSTRUMENT

(75) Inventor: Stanislaw Kostrzewski, Newtown, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 55 days.

(21) Appl. No.: 12/751,198

(22) Filed: Mar. 31, 2010

(65) Prior Publication Data

US 2011/0240712 A1  Oct. 6, 2011

(51) Int. Cl.
*A61B 17/068* (2006.01)

(52) U.S. Cl. ........ 227/176.1; 227/19; 606/139; 606/219

(58) Field of Classification Search ............... 227/19, 227/176.1, 175.1, 175.2, 180.1; 606/139, 606/153, 219
See application file for complete search history.

(56) References Cited

U.S. PATENT DOCUMENTS

| | | |
|---|---|---|
| 4,869,414 A | 9/1989 | Green et al. |
| 5,312,023 A | 5/1994 | Green et al. |
| 5,326,013 A | 7/1994 | Green et al. |
| 5,330,502 A | 7/1994 | Hassler et al. |
| 5,374,277 A | 12/1994 | Hassler |
| 5,381,943 A | 1/1995 | Allen et al. |
| 5,383,888 A | 1/1995 | Zvenyatsky et al. |
| 5,403,342 A | 4/1995 | Tovey et al. |
| 5,405,344 A | 4/1995 | Williamson et al. |
| 5,409,498 A | 4/1995 | Braddock et al. |
| 5,411,519 A | 5/1995 | Tovey et al. |
| 5,417,203 A | 5/1995 | Tovey et al. |
| 5,456,684 A | 10/1995 | Schmidt et al. |
| 5,474,571 A | 12/1995 | Lang |
| 5,497,933 A | 3/1996 | DeFonzo et al. |
| 5,944,723 A | 8/1999 | Colleran et al. |
| 5,993,384 A | 11/1999 | Lunsford et al. |
| 6,350,269 B1 | 2/2002 | Shipp et al. |
| 6,652,539 B2 | 11/2003 | Shipp et al. |
| 6,652,545 B2 | 11/2003 | Shipp et al. |
| 6,666,854 B1 | 12/2003 | Lange |
| 6,679,886 B2 | 1/2004 | Weikel et al. |
| 6,752,756 B2 | 6/2004 | Lunsford et al. |
| 6,755,338 B2 | 6/2004 | Hahnen et al. |
| 6,830,174 B2 | 12/2004 | Hillstead et al. |
| 6,830,546 B1 | 12/2004 | Chin et al. |
| 7,090,689 B2 | 8/2006 | Nagase et al. |

(Continued)

FOREIGN PATENT DOCUMENTS

EP  1 693 008 A1  8/2006

(Continued)

OTHER PUBLICATIONS

European Search Report for EP 11250406.3-2310 date of completion is Jul. 5, 2011 (3 pages).

*Primary Examiner* — Scott A. Smith

(57) ABSTRACT

A surgical instrument is provided. The surgical instrument includes a housing. The surgical instrument includes an elongated portion extending distally from the housing and defines a longitudinal axis. An end effector operably couples to the elongated portion. A first pivoting member pivotably couples to a distal end of the elongated portion. The first pivoting member defines a first pivot axis intersecting the longitudinal axis when the first pivoting member is rotated. A distal mounting assembly pivotably couples to the first pivoting member and operably couples to the end effector. The distal mounting assembly defines a second pivot axis intersecting the first pivot axis and the longitudinal axis when the proximal mounting assembly is rotated.

25 Claims, 4 Drawing Sheets

U.S. PATENT DOCUMENTS

| | | |
|---|---|---|
| 7,147,650 B2 | 12/2006 | Lee |
| 7,207,997 B2 | 4/2007 | Shipp et al. |
| 7,241,288 B2 | 7/2007 | Braun |
| 7,241,289 B2 | 7/2007 | Braun |
| 7,326,178 B1 | 2/2008 | Lunsford et al. |
| 7,328,828 B2 | 2/2008 | Ortiz et al. |
| 7,338,513 B2 | 3/2008 | Lee et al. |
| 7,354,447 B2 | 4/2008 | Shelton, IV et al. |
| 7,364,060 B2 | 4/2008 | Milliman |
| 7,364,582 B2 | 4/2008 | Lee |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,431,189 B2 | 10/2008 | Shelton, IV et al. |
| 7,438,209 B1 | 10/2008 | Hess et al. |
| 7,441,684 B2 | 10/2008 | Shelton, IV et al. |
| 7,442,195 B1 | 10/2008 | Behrens |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,476,198 B1 | 1/2009 | Chin et al. |
| 7,476,226 B2 | 1/2009 | Weikel et al. |
| 7,490,749 B2 | 2/2009 | Schall et al. |
| 7,494,499 B2 | 2/2009 | Nagase et al. |
| 7,500,979 B2 | 3/2009 | Hueil et al. |
| 7,503,474 B2 | 3/2009 | Hillstead et al. |
| 7,506,791 B2 | 3/2009 | Omaits et al. |
| 7,549,564 B2 | 6/2009 | Boudreaux |
| 7,549,998 B2 | 6/2009 | Braun |
| 7,553,275 B2 | 6/2009 | Padget et al. |
| 7,556,186 B2 | 7/2009 | Milliman |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,572,266 B2 | 8/2009 | Young et al. |
| 7,575,144 B2 | 8/2009 | Ortiz et al. |
| 7,582,095 B2 | 9/2009 | Shipp et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,517 B2 | 11/2009 | Lim |
| 7,615,066 B2 | 11/2009 | Dauitz et al. |
| 7,615,067 B2 | 11/2009 | Lee et al. |
| 7,644,848 B2 | 1/2010 | Swayze et al. |
| 7,648,519 B2 | 1/2010 | Lee et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,284 B2 | 3/2010 | Padget et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,678,117 B2 | 3/2010 | Hinman et al. |
| 7,678,125 B2 | 3/2010 | Shipp |
| 7,682,307 B2 | 3/2010 | Danitz et al. |
| 7,879,070 B2 * | 2/2011 | Ortiz et al. .................. 606/205 |
| 7,891,533 B2 * | 2/2011 | Green et al. ................ 227/176.1 |
| 7,891,632 B2 * | 2/2011 | Rucinski et al. ............. 248/447 |
| 7,896,890 B2 * | 3/2011 | Ortiz et al. .................. 606/139 |
| 7,905,380 B2 * | 3/2011 | Shelton et al. ............. 227/178.1 |

FOREIGN PATENT DOCUMENTS

| | | |
|---|---|---|
| EP | 1 854 418 A1 | 11/2007 |
| EP | 1 915 957 A2 | 4/2008 |
| EP | 1 997 440 A2 | 12/2008 |
| EP | 2 005 902 A2 | 12/2008 |

* cited by examiner

SURGICAL INSTRUMENT

BACKGROUND

1. Technical Field

This application relates to surgical instruments, and more particularly, to surgical instruments configured to articulate.

2. Background of Related Art

Surgical instruments configured to articulate are well known in the medical art. For example, one type of surgical instrument includes an end effector configured for articulation and configured to join tissue (e.g., surgical stapler, electrosurgical forceps, or other suitable device). Typically, such surgical instruments include a shaft extending from a handle and/or trigger assembly, an end effector assembly including a pair of opposing jaw members, and an approximation mechanism for approximating the jaw members. In some instances, a drive or knife bar (or other suitable device) operably couples to a knife blade and, collectively, are configured to sever tissue that has been joined (e.g., stapled and/or sealed). Typically one or both of the jaw members is adapted to receive the knife blade within a knife channel operably disposed on one or both of the opposing jaw members.

In the instance where the surgical instrument is a surgical stapler, one of the jaw members may support an anvil assembly and the other jaw member may support a cartridge assembly. In certain instances, a knife blade is translatable through a respective knife channel operably disposed with each of the anvil and cartridge assemblies. In some instances, the surgical stapler may be adapted to connect to a loading unit (e.g., disposable loading unit (DLU) or single use loading unit (SULU)) that includes an end effector assembly, which includes anvil assembly and a cartridge assembly for supporting a plurality of surgical fasteners.

In the instance where the surgical instrument is an electrosurgical forceps, one or both of the jaw members may support a seal plate. In certain instances, a knife blade is translatable through a respective knife channel operably disposed with each of opposing jaw members.

There may exist one or more practical challenges associated with surgical instruments that include articulation devices configured to rotate of one or more components (e.g., an end effector) associated with the surgical instruments. More particularly, the range of motion (e.g., amount of rotation) associated with the articulation device may be limited. This limited range of motion of the articulation device may inhibit and/or prevent the end effector and/or jaw members associated therewith from functioning in a manner as intended. That is, the jaw members of the end effector may not properly and/or effectively grasp tissue, which, in turn, may result in the jaw members providing an effect to the grasped tissue that is less than desirable, e.g., an incomplete formation of ejected staples within tissue, an incomplete seal of tissue, etc. In addition, the limited range of motion of the articulation device results in a radius of curvature adjacent the articulation device that is relatively small when the end effector is in an articulated position, such as, for example, when the en effector is rotated at an angle of 45°. Thus, in the instance where a drive or knife bar is required to push a knife blade, the small radii of curvature adjacent the articulation device may cause permanent knife bar deflection.

SUMMARY

According to an aspect of the present disclosure, a surgical instrument configured to surgically join tissue is provided. The surgical instrument includes a housing. The surgical instrument includes an elongated portion extending distally from the housing and defines a longitudinal axis. An end effector operably couples to the elongated portion. A proximal mounting assembly pivotably couples to a distal end of the elongated portion. The proximal mounting assembly defines a first pivot axis intersecting the longitudinal axis. A stationary gear is provided and is coupled to the elongated portion so that the proximal mounting portion is pivotable with respect to the longitudinal axis. A distal mounting assembly pivotably couples to the proximal mounting assembly and couples to the end effector. A movable gear is coupled to the end effector, the distal mounting assembly being pivotable with respect to the proximal mounting assembly. An articulation member is coupled to the proximal mounting assembly so that movement of the articulation member pivots the proximal mounting assembly and the distal mounting assembly with respect to the longitudinal axis.

In an embodiment, the movable gear is in operative engagement with the stationary gear. At least one link may be provided to operably couple the proximal mounting assembly to the distal mounting assembly. The at least one link is pivotably connected to the elongated portion.

In an embodiment, the stationary gear is formed on a pivot plate coupled to the elongated portion. At least one link may couple the proximal mounting assembly to the distal mounting assembly, a proximal portion of the at least one link being movable within an arcuate recess formed in the pivot plate.

In an embodiment, rotation of the proximal mounting assembly in a clockwise direction, and the interaction between the stationary gear and the movable gear, causes rotation of the distal mounting assembly in the clockwise direction.

In one particular embodiment, the end effector includes a first jaw member and a second jaw member, the first jaw member and second jaw member being movable from an open position wherein the jaw members are disposed in spaced relation relative to one another, to a clamping position wherein the jaw members are in an approximated position relative to one another.

In one particular embodiment, the end effector includes a staple cartridge assembly and an anvil assembly.

According to an aspect of the present disclosure a loading unit configured for use with a surgical instrument is provided. A first pivoting member pivotably couples to the loading unit. The first pivoting member defines a first pivot axis intersecting a longitudinal axis defined by the loading unit. A second pivoting member pivotably couples to the first pivoting member and operably couples to an end effector associated with the loading unit. The second pivoting member defines a second pivot axis that moves from a position aligned with the longitudinal axis to a position offset from the longitudinal axis when the first pivoting member is rotated. A movable interface between the first pivoting member and the second pivoting member.

In an embodiment, a stationary gear is coupled to a proximal end of the loading unit. In an embodiment, a movable gear couples the second pivoting member to the end effector, the movable gear in operative engagement with the stationary gear and forms the movable interface.

In an embodiment, rotation of the first pivoting member in a clockwise direction, and the interaction between the stationary gear and the movable gear, causes rotation of the second pivoting member in the clockwise direction.

In one particular embodiment, the end effector includes a first jaw member and a second jaw member wherein the first jaw member and second jaw member are movable from an open position wherein the jaw members are disposed in spaced relation relative to one another, to a clamping position wherein the jaw members are approximated relative to one another.

In one particular embodiment, the end effector includes a staple cartridge assembly and an anvil assembly.

In a further aspect, a surgical instrument configured to surgically join tissue is provided. The surgical instrument includes a housing. The surgical instrument includes an elongated portion extending distally from the housing and defines a longitudinal axis. An end effector operably couples to the elongated portion. A first pivoting member pivotably couples to a distal end of the elongated portion. The first pivoting member defines a first pivot axis intersecting the longitudinal axis. A stationary gear is provided and is coupled to the elongated portion so that the proximal mounting portion is pivotable with respect to the longitudinal axis. A second pivoting member pivotably couples to the first pivoting member and couples to the end effector. A movable gear is coupled to the end effector, the second pivoting member being pivotable with respect to the first pivoting member. An articulation member is coupled to the first pivoting member so that movement of the articulation member pivots the first pivoting member and the second pivoting member with respect to the longitudinal axis.

In an embodiment, the movable gear is in operative engagement with the stationary gear. At least one link may be provided to operably couple the first pivoting member to the second pivoting member. The at least one link is pivotably connected to the elongated portion.

In an embodiment, the stationary gear is formed on a pivot plate coupled to the elongated portion. At least one link may couple the first pivoting member to the second pivoting member, a proximal portion of the at least one link being movable within an arcuate recess formed in the pivot plate.

In an embodiment, rotation of the first pivoting member in a clockwise direction, and the interaction between the stationary gear and the movable gear, causes rotation of the second pivoting member in the clockwise direction.

In one particular embodiment, the end effector includes a first jaw member and a second jaw member, the first jaw member and second jaw member being movable from an open position wherein the jaw members are disposed in spaced relation relative to one another, to a clamping position wherein the jaw members are in an approximated position relative to one another.

In one particular embodiment, the end effector includes a staple cartridge assembly and an anvil assembly.

BRIEF DESCRIPTION OF THE DRAWINGS

Various embodiments of the present disclosure are described herein with reference to the drawings wherein.

DETAILED DESCRIPTION

Figure 1A:
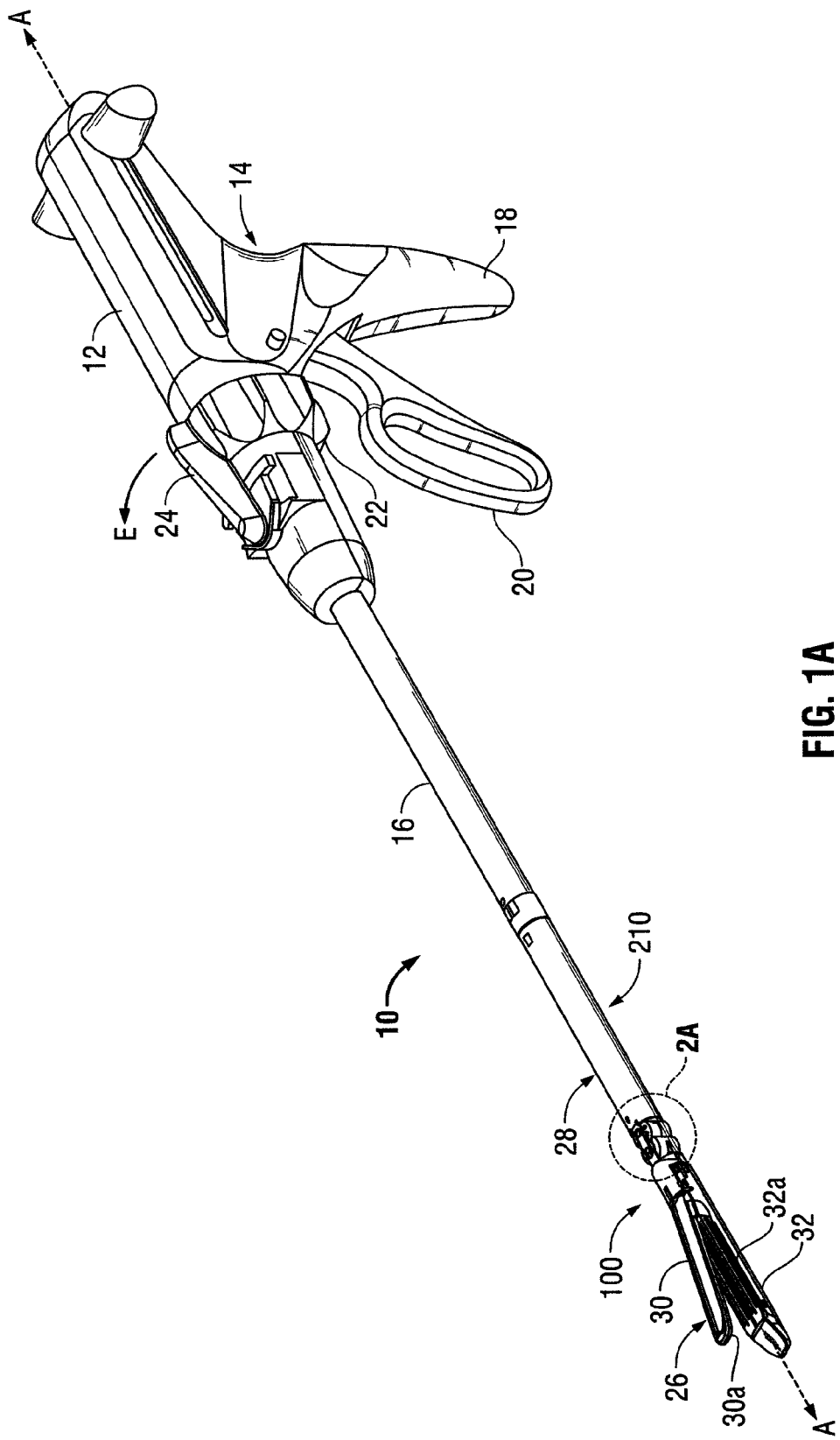
FIG. 1A is a perspective view of a surgical instrument including a loading unit adapted for use with an articulation assembly in accordance with an embodiment of the present disclosure.

Embodiments of the presently disclosed surgical instrument are described in detail with reference to the drawings, wherein like reference numerals designate similar or identical elements in each of the several views. In the drawings and the description that follows, the term "proximal" refers to the end of the surgical stapling instrument that is closest to the handle assembly, whereas the term "distal" refers to the end of the surgical stapling instrument that is farthest from the handle assembly. As appreciated by one skilled in the art, the depicted surgical stapling instrument fires staples, but it may be adapted to fire any other suitable fastener such as clips and two-part fasteners.

FIG. 1A illustrates a surgical instrument 10 with an articulation assembly 100 in accordance with the present disclosure. Briefly, surgical instrument 10 (e.g., a surgical stapler 10) includes a housing 12 having a handle assembly 14 and an elongated portion or shaft 16 defining a longitudinal axis "A-A". Handle assembly 14 includes a stationary handle member 18, and a movable handle member 20. A rotatable member 22 is mounted on the handle assembly 14 to facilitate rotation of elongated portion 16 with respect to handle assembly 14. An articulation lever 24 is also mounted on handle assembly 16 to facilitate articulation of an end effector 26. The distal end of instrument 10 may be configured as a loading unit 28 (e.g., a disposable loading unit (DLU) or a single use loading unit (SULU)) that is releasably secured to a distal end of shaft 16. In other embodiments, the jaws of the instrument are attached to the elongated portion or shaft 16 and a replaceable cartridge is utilized. Loading unit 28 includes end effector 26 including a pair of opposing first and second jaw members 30 and 32, respectively, including a respective anvil assembly 30a having a plurality of staple forming pockets and cartridge assembly 32a housing a plurality of surgical staples. In embodiments, one or both of the cartridge assembly 28 and anvil assembly 30 may be configured to conduct electrosurgical energy.

For a more detailed description of the operation of surgical instrument 10 reference is made to commonly-assigned U.S. Pat. No. 5,865,361 to Milliman et al., the entire contents of which is incorporated herein by reference.

Figure 1B:
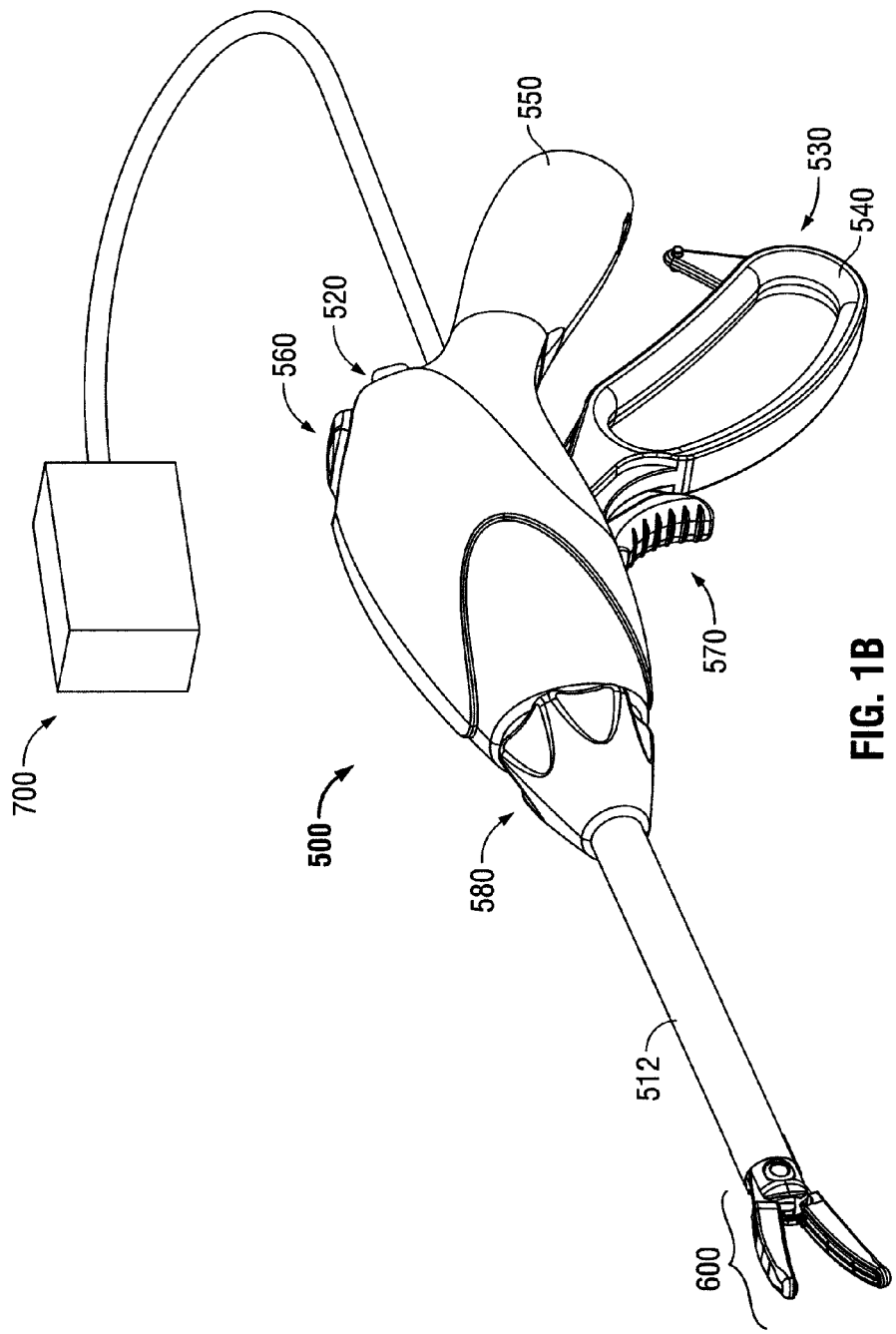
FIG. 1B is perspective view of an electrosurgical instrument adapted for use with an articulation assembly in accordance with an embodiment of the present disclosure.

Articulation assembly 100 may be adapted for use with an electrosurgical instrument 500, e.g., an endoscopic electrosurgical forceps 500 (FIG. 1B). Briefly, the electrosurgical instrument 500 can be any suitable type of electrosurgical instrument, including but not limited to electrosurgical instruments that can grasp and/or perform any of the above mentioned electrosurgical procedures. One type of electrosurgical instrument may include an endoscopic electrosurgical forceps 500 as disclosed in United States Patent Publication No. 2007/0173814 entitled "Vessel Sealer and Divider for Large Tissue Structures," the contents of which is incorporated in its entirety by reference. A brief discussion of endoscopic electrosurgical forceps 500 and components, parts, and members associated therewith is included herein to provide further detail and to aid in the understanding of the present disclosure.

Electrosurgical forceps 500 is shown for use with various electrosurgical procedures (e.g., tissue sealing procedure) and generally includes a housing 520, a handle assembly 530 that includes a movable handle 540 and a fixed handle 550, a rotating assembly 580, a push button assembly 560, a trigger assembly 570, a shaft 512, and an end effector assembly 600, which mutually cooperate to grasp, seal and divide large tubular vessels and large vascular tissues. In embodiments, electrosurgical forceps 500 is adapted to connect to an electrosurgical energy source 700. Although the majority of the figure drawings depict an electrosurgical forceps 500 for use in connection with laparoscopic surgical procedures, the present disclosure may be used for more traditional open surgical procedures or endoscopic procedures.

Stapling instrument 10 and electrosurgical instrument 500 hereinafter will be collectively referred to as a surgical instrument 10. In the description that follows, the articulation assembly 100 will be described in terms of use with a surgical instrument 10 including the components associated with the surgical instrument depicted in FIG. 1A.

Figure 2A:
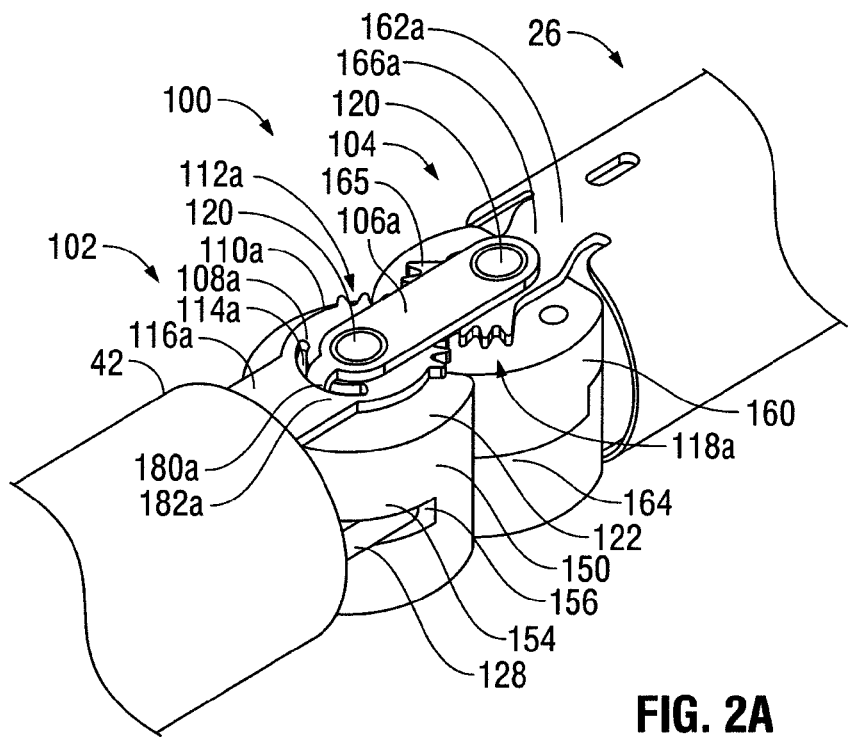
FIG. 2A is an enlarged view of the area of the detail in FIG. 1A with the articulation assembly in a non-articulation condition.

Referring now to FIGS. 2A-4, and initially with reference to FIG. 2A, an embodiment of the articulation assembly 100 is shown. In the embodiment illustrated in FIGS. 2A-4, a proximal end of a loading unit 28 is configured to releasably secure to a distal end of the elongated shaft 14 of the surgical instrument 10 (FIG. 1A).

Figure 4:
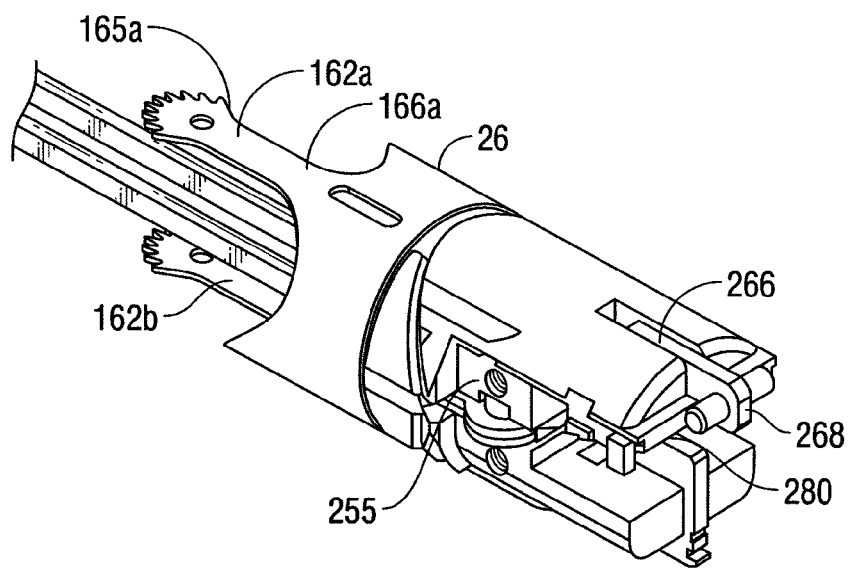
FIG. 4 is an enlarged perspective view, with portions broken away, of a distal portion of a distal mounting assembly of the disposable loading unit shown in FIG. 1A.

With continued reference to FIG. 2A, articulation assembly 100 provides increased articulation of the end effector 26 when compared to currently known articulation assemblies. In addition, the articulation assembly 100 provides bending of a knife bar 266 (a portion of which is shown in FIG. 4, for example) along a larger radius of curvature, thus minimizing the stress on a knife bar 266, which, in turn, impedes and/or prevents permanent deflection of the knife bar 266.

Figure 2B:
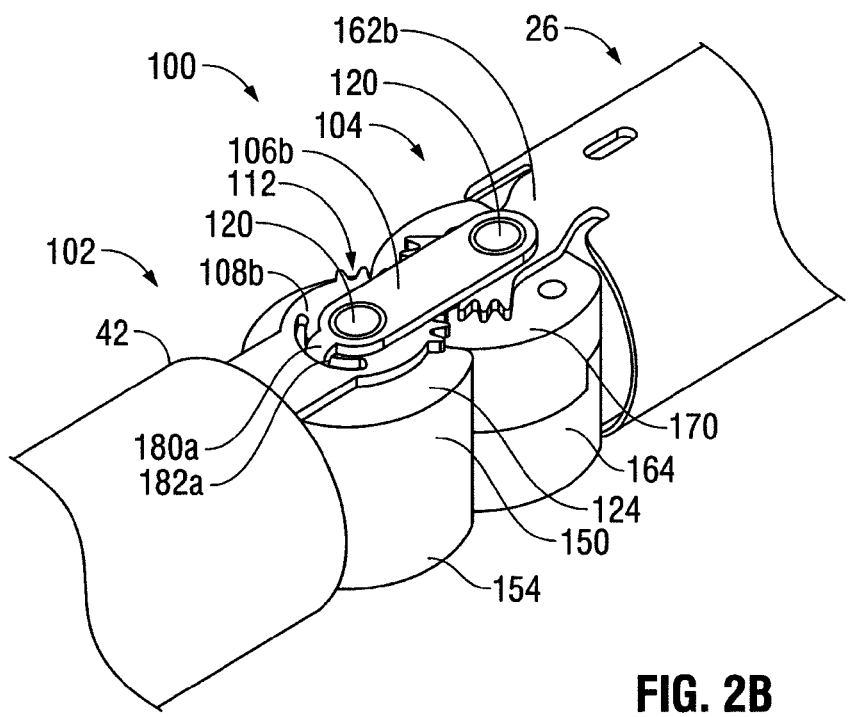
FIG. 2B is a bottom perspective view of the articulation assembly depicted in FIG. 2A.

Articulation assembly 100 includes a proximal mounting assembly 102 and a distal mounting assembly 104 operably coupled to each other by at least one link, such as a pair of links 106a and 106b (see FIG. 2A in combination with FIG. 2B).

Figure 3:
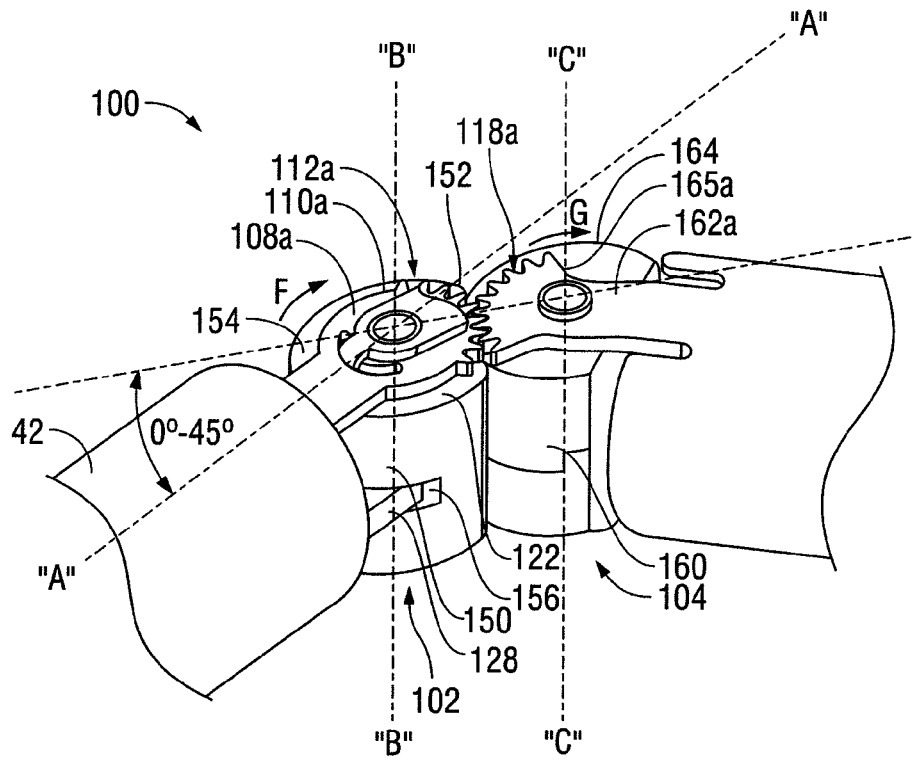
FIG. 3 is an enlarged perspective view, with portions broken away, of the articulation assembly depicted in FIG. 1A with the articulation assembly in an articulated condition.

Proximal mounting assembly 102 defines a first vertical pivot axis "B-B" through the proximal mounting assembly (see FIG. 3, for example) and includes a pivoting member 150 rotatable from about 0° to about 45°, or about 90°, on either side, off of the longitudinal axis "A-A", see FIG. 3, for example. Pivoting member 150 includes proximal and distal ends that operably communicate with one or more components associated with the loading unit 28 and the distal mounting assembly 104. More particularly, pivoting member 150 includes a generally circumferential configuration having arcuate proximal and distal ends 154 and 152, respectively, that facilitate rotation of the pivoting member 150 about axis B-B and with respect to a distal end 42 of the loading unit 28 and the distal mounting assembly 104 (see FIG. 2A or 2B and FIG. 3). More particularly, distal end 152 includes a radius of curvature of suitable proportion for transitioning the pivoting member 150, and/or other operative components associated with the proximal mounting assembly 102, from a non-articulated position to an articulated position (see FIG. 2A showing the non-articulated position and see FIG. 3 showing the articulated position). Pivoting member 150 includes an arcuate or convex proximal end 154 also having a radius of curvature of suitable proportion for transitioning the pivoting member 150, and/or other operative components associated with the proximal mounting assembly 102, from a non-articulated position to an articulated position (see FIG. 2A in combination with FIG. 3). An elongated groove or channel 156 is positioned alongside of the pivoting member 150. In the embodiment illustrated in FIGS. 2A and 3, the elongated channel 156 extends along a right side of the pivoting member 150 between a proximal and distal face 122 and 124, respectively, of the pivoting member 150. Alternatively, the elongated channel 156 may be positioned along a left side of the pivoting member 150. Elongated channel 156 is proportioned to receive a distal end of an articulation member 128, which may be configured as a rod, strap, cable, or other member. One or more structures, e.g., a pivot pin (not explicitly shown), operably associated with the pivoting member 150 and positioned in the elongated channel 156, couples to the distal end of the articulation rod 128. For a more detailed description of the articulation member, reference is made to U.S. Pat. No. 5,865,361 to Milliman et al.

Proximal mounting assembly 102 couples to distal end 42 of the loading unit 28. More particularly, pivoting member 150 is mounted between upper and lower pivot plates 108a and 108b, respectively, such that the pivoting member 150 is rotatable relative to each of the upper pivot plate 108a and lower pivot plate 108b, and the distal end 42 of the loading unit 28. The upper and lower pivot plates 108a and 108b, respectively, are identical to each other, thus, and unless otherwise noted, only the operative features of the upper pivot plate 108a will be described herein. Upper pivot plate 108a includes an elongated proximal end 116a that tapers proximally and fixedly attaches to the distal end 42 of the loading unit 28. In the embodiment illustrated in FIGS. 2A-3, at least a portion of the proximal end 116a fixedly attaches to the distal end 42 of a shaft of the loading unit 28 via welding, one or more rivets, adhesive, or other attachment method. Upper pivot plate 108a extends distally toward the end effector 26 and defines a stationary gear. The stationary gear can be configured as a curved or circumferential distal end 110a having a plurality of teeth 112a that are configured to mesh or engage with a corresponding plurality of teeth 118a associated with the distal mounting assembly 104 (as best seen in FIG. 3). Upper pivot plate 108a is stationary in that upper pivot plate 108a remains parallel to the longitudinal axis "A-A" during rotation of the proximal mounting assembly 102 (see FIG. 2A in combination with FIG. 3). One or more pivot pins 120 (or other suitable structure) is operably associated with the proximal mounting assembly 102 and pivotably couples the pivoting member 150 to respective upper and lower pivot plates 108a and 108b. More particularly, the pivot pin 120 extends from an upper face 122 of the pivoting member 150 through the upper pivot plate 108a and to a corresponding link 106a (FIG. 2A). Likewise, a pivot pin 120 extends from a distal face 124 of the pivoting member 150 through the lower pivot plate 108b and to a corresponding link 106b (FIG. 2B). Upper pivot plate 108a includes an arcuate or concave recess or slot 114a operably disposed adjacent proximal end 116a of upper pivot plate 108a. Slot 114a is configured and proportioned to house a proximal portion of a corresponding link 106a, to be described in greater detail below. Slot 114a provides additional structural integrity to and a smooth transition for the proximal mounting assembly 102 when the components of the proximal mounting assembly 102 are rotated.

As noted above, an articulation member 128 is operably associated with the loading unit 28. More particularly, the articulation member 128 is in mechanical communication with the articulation lever 24. Articulation member 128 couples to the pivoting member 150 of the proximal mounting assembly 102 and controls the rotation of the proximal mounting assembly 102. In the embodiment illustrated in FIGS. 2A and 3, the articulation member 128 extends along a length of the loading unit 28 from a proximal end where the loading unit 28 couples to a distal end of the surgical instrument 10 to the distal portion 42. For a more detailed description of the structural and functional features of articulation rod 128, and operative components associated therewith, reference is again made to U.S. Pat. No. 5,865,361 to Milliman et al.

Distal mounting assembly 104 defines a second vertical pivot axis "C-C." The distal mounting assembly includes a pivoting member 160 rotatable about the axis C-C so that the pivoting member 160 articulates with respect to the longitudinal axis (FIG. 3). Pivoting member 160 includes a proximal end that operably communicates with the pivoting member 150 of proximal mounting assembly 102. More particularly, pivoting member 160 includes a generally curved or circumferential configuration having an arcuate proximal end 164 that facilitates rotation of the pivoting member 160 with respect to the longitudinal axis. More particularly, proximal end 164 includes a radius of curvature of suitable proportion for transitioning the pivoting member 160, and/or other operative components associated with the distal mounting assembly 104, from a non-articulated position to an articulated position (see FIG. 2A in combination with FIG. 3).

In the embodiments illustrated in FIGS. 2A-3, the distal end 152 of pivoting member 150 and proximal end 164 of the pivoting member 160 are configured as complementary surfaces. Thus, in an embodiment, the distal 152 of pivoting member 150 may include a convex configuration and proximal end 164 of the pivoting member 160 may include a concave configuration. Other complementary surfaces are contemplated and within the purview of the present disclosure.

Distal mounting assembly 104 operably couples to the end effector 26 of the loading unit 28. In the embodiment illustrated in FIGS. 2A-4, distal mounting assembly 104 is rigidly attached to a proximal end of the anvil assembly 30a associated with the first jaw member 30 (see FIG. 4, for example). More particularly, pivoting member 160 is rigidly attached to the anvil assembly 30a between upper and lower pivot plates 162a and 162b (see FIGS. 2A and 2B in combination with FIG. 4). The upper and lower pivot plates 162a and 162b, respectively, are identical to each other, thus, and unless otherwise noted, only the operative features of the upper pivot plate 162a will be described herein. Upper pivot plate 162a includes an elongated distal end 166a that extends distally and fixedly attaches to the anvil assembly 30a of the loading unit 28 by any suitable methods and/or structures. In the embodiment illustrated in FIGS. 2A, 3 and 4, upper pivot plate 162a is monolithically formed with the proximal end of the proximal end of the end effector. Alternatively, the upper pivot plate 162a may couple to the anvil assembly 30a by welding, one or more rivets, adhesive, or the like. Upper pivot plate 162a is in general alignment with and extends proximally toward the corresponding upper pivot plate 108a associated with the proximal mounting assembly 102. The upper pivot plate 162a defines a movable gear configured as a generally curved or circumferential proximal end 165a having a plurality of teeth 118a that is configured to mesh or engage with the corresponding plurality of teeth 112a associated with the stationary gear of the proximal mounting assembly 102. Upper pivot plate 162a is movable in that upper pivot plate 162a is not parallel with respect to the longitudinal axis "A-A" during rotation of the proximal mounting assembly 102 and the distal mounting assembly 104 (see FIG. 2A in combination with FIG. 3). One or more pivot pins 120 (or other suitable structure) is operably associated with the distal mounting assembly 104 and pivotably couples the pivoting member 160 to respective upper and lower pivot plates 162a and 162b. More particularly, the pivot pin 120 extends from an upper face 168 of the pivoting member 160 through the upper pivot plate 162a and to a corresponding link 106a (FIG. 2A). Likewise, a pivot pin 120 extends from a lower face 170 of the pivoting member 160 through the lower pivot plate 162b and to a corresponding link 106b (FIG. 2B).

A pair of links 106a and 106b operably couples the proximal mounting assembly 102 and distal mounting assembly 104 to each other. Links 106a and 106b are identical to each other, thus, and unless otherwise noted, only the operative features of the link 106a will be described herein. Link 106a is of rigid construction and operably couples the proximal and distal mounting assemblies 102 and 104, respectively, to each other via the pivot pins 120, see FIGS. 2A and 2B. A proximal end 180a of the link 106a is movable within the corresponding slot 114a. More particularly, a finger portion 182a movably passes through the slot 114a such that the link 106a may be rotated from either side of the longitudinal axis "A-A," see FIG. 2A in combination with FIG. 3, for example. The proximal end of the link 106a passes through the slot 114a and is connected to the pivoting member 150, and the lower link is similarly connected.

In operation, both the proximal pivoting member 150 and the distal pivoting member 160 rotate with respect to the longitudinal axis. The movement of the proximal pivoting member 150 drives the movement of the distal pivoting member 160. The links 106a and 106b are rigidly connected with the proximal pivoting member 150 and rotate with respect to the plates 108.

In other embodiments, the concave/convex surfaces on the proximal pivoting member 150 and distal pivoting member 160 are relied upon to drive the rotation of the distal pivoting member. In embodiments including the gears on the pivot plates, the relative movement between the proximal and the distal pivot members depends on the gear ratio. For example, a proximal pivot plate with 28 gear teeth and a distal pivot plate with 20 gear teeth have a gear ratio of 1.4. The gear ratio is used to produce a greater degree of articulation for the end effector for the degree of movement of the proximal pivot member.

Turning now to FIG. 4, in an embodiment, loading unit 28 includes an axial drive assembly that includes an elongated drive beam or knife bar 266 including a distal working head 268 defined by a vertical support strut that supports or incorporates a knife blade 280. Knife bar 266 may be constructed from a single sheet of material or multiple stacked sheets. Knife blade 280 is positioned to translate slightly behind an actuation sled (not shown) through a central longitudinal slot in cartridge assembly 28a, and drive the sled forward when the movable handle of the housing is actuated. The actuation sled, as disclosed in Milliman, et al., U.S. Pat. No. 5,865,361, which is incorporated by reference herein in its entirety, has angled surfaces for camming staple pusher. As the staple pushers are disposed in the staple cartridge so that they support surgical staples, the forward movement of the sled (which is driven by the knife bar 266) cams the staple pushers upwardly driving the staples against an anvil surface of the anvil assembly. In this way, surgical staples are placed in, and formed in tissue, while the blade 280 divides the tissue.

The knife bar 266 is relatively flexible so that, when the instrument 10 is fired in the articulated position, the knife bar 266 bends. In this case, the knife bar 266 bends around both of the pivots 120. A pair of blow out plates 255 are positioned on either side of the pivots 120, extending from one end of the articulation assembly 100 to the other end of the articulation assembly, to prevent outward bulging of the drive assembly, e.g., the knife bar 266, during articulation and firing of tool assembly 20. In certain embodiments, a pair of blow out plates 255 are positioned on either side of the proximal pivot 120 and another pair of blow out plates are positioned on either side of the distal pivot 120.

Reference is again made to FIG. 2A in combination with FIG. 3. In operation, the proximal mounting assembly 102 functions as an articulation multiplier when the proximal mounting assembly 102 is rotated. That is, rotation of the pivoting member 150, in combination with the links 106a and 106b and the gears associated with each of the proximal and distal mounting assemblies 102 and 104, respectively, cause the distal mounting assembly 104 including the pivoting member 160 and, thus, the end effector 26 to pivot about the proximal mounting assembly 102 and/or the pivoting member 150. As can be appreciated by one of skill in the art, the links 106a and 106b in combination with the gear configurations associated with each of the proximal and distal mounting assemblies 102 and 104 function not unlike that of a planetary gear system. The gear ratio between the gears of the proximal and distal mounting assemblies 102 and 104, respectively, determines the amount of relative motion between the proximal and distal mounting assemblies 102 and 104, respectively. More particularly, a high gear ratio provides a high degree of relative rotation between the respective proximal and distal mounting assemblies 102 and 104, while a low gear ratio provides a low degree of relative rotation between the respective proximal and distal mounting assemblies 102 and 104. In the embodiment illustrated in FIGS. 2A-3, the proximal and distal mounting assemblies 102 and 104, respectively, include a 1:1 gear ratio.

In use, the articulation lever 24 is rotated by the user of the instrument, in the direction of directional arrow E (FIG. 1A). Rotation of articulation lever 24 translates the articulation member 128 in a proximal direction. This movement of the articulation member 128 rotates the proximal mounting assembly 102 around the associated pivot 120 and in the direction of directional arrow F (FIG. 3). The interaction between the stationary gear and the movable gear causes the distal mounting assembly 104 and, thus, the end effector 26 to rotate off the longitudinal axis A-A, in the direction of directional arrow G (FIG. 3). Accordingly, the amount of articulation that the end effector 26 is capable of achieving is increased when compared to an amount of articulation that known end effectors are capable of achieving. More particularly, known end effectors are capable of articulating an amount that is approximately equal to the amount of articulation that pivoting member 150 of proximal mounting assembly 102 is capable of pivoting. In accordance with the present disclosure, and as noted above, rotation of the pivoting member 150, in combination with the links 106a and 106b and gear configurations associated with each of the proximal and distal mounting assemblies 102 and 104, respectively, cause the pivoting member 160 and, thus, the end effector 26 to pivot an additional amount about the proximal mounting assembly 102 and/or the pivoting member 150. As a direct result thereof, the amount of articulation that end effector 26 is capable of achieving is increased, which, as can be appreciated by one of ordinary skill in the art may provide a user with a better mechanical advantage when manipulating tissue of interest. Either the configuration of the cooperating surfaces on the pivoting member 150 and pivoting member 160, or the gears (or other cooperating shape on the pivoting plates) can be relied upon to produce the articulating movement of the distal pivoting member 160. Further, in other embodiments, the articulation member can be arranged to move distally in order to produce the articulating movement.

From the foregoing and with reference to the various figures, those skilled in the art will appreciate that certain modifications can also be made to the present disclosure without departing from the scope of the same. For example, in an embodiment, the gear configurations of each of the proximal and distal mounting assemblies 102 and 104, respectively, may be configured to cause the proximal and distal mounting assemblies 102 and 104, respectively, to move in opposite directions. That is, one of the mounting assemblies (e.g., mounting assembly 102) may be configured to rotate in the direction of directional arrow F, i.e., clockwise, while the other mounting assembly (e.g., mounting assembly 104) may be configured to rotate in a direction opposite that of directional arrow G, i.e., counter clockwise. In embodiments, a third gear is disposed between the stationary gear and the distal movable gear, mounted in the middle of the link 106. This would result in the distal pivot member rotating in the opposite direction of the proximal pivot member.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
   a housing;
   an elongated portion extending distally from the housing and defining a longitudinal axis;
   an end effector operably coupled to the elongated portion;
   a proximal mounting assembly pivotably coupled to a distal end of the elongated portion, the proximal mounting assembly defining a first pivot axis intersecting the longitudinal axis;
   a stationary gear coupled to the elongate portion, the proximal mounting assembly being pivotable with respect to the stationary gear;
   a distal mounting assembly pivotably coupled to the proximal mounting assembly and coupled to the end effector, the distal mounting assembly defining a second pivot axis;
   a movable gear coupled to the end effector, the distal mounting assembly being pivotable with respect to the proximal mounting assembly; and
   an articulation member coupled to the proximal mounting assembly so that movement of the articulation member pivots the proximal mounting assembly and the distal mounting assembly with respect to the longitudinal axis.

2. A surgical instrument according to claim 1, wherein the movable gear is in operative engagement with the stationary gear.

3. A surgical instrument according to claim 1, wherein at least one link operably couples the proximal mounting assembly to the distal mounting assembly.

4. A surgical instrument according to claim 3, wherein the at least one link is pivotably connected to the elongated portion.

5. A surgical instrument according to claim 1, wherein the stationary gear is formed on a pivot plate coupled to the elongated portion.

6. A surgical instrument according to claim 5, wherein at least one link couples the proximal mounting assembly to the distal mounting assembly, a proximal end of the at least one link being movable within an arcuate recess formed in the pivot plate.

7. A surgical instrument according to claim 1, wherein rotation of the proximal mounting assembly in a clockwise direction, and the interaction between the movable gear and the stationary gear, causes rotation of the distal mounting assembly in the clockwise direction.

8. A surgical instrument according to claim 1, wherein the end effector includes a first jaw member and a second jaw member, the first jaw member and the second jaw member being movable from an open position wherein the jaw members are disposed in spaced relation relative to one another, to a clamping position wherein the jaw members are approximated relative to one another.

9. A surgical instrument according to claim 8, wherein the end effector includes a staple cartridge assembly and an anvil assembly.

10. A loading unit configured for use with a surgical instrument, the loading unit comprising:
a first pivoting member pivotably coupled to the loading unit, the first pivoting member defining a first pivot axis intersecting a longitudinal axis defined by the loading unit, the first pivot axis being aligned with the longitudinal axis;
a second pivoting member pivotably coupled to the first pivoting member and operably coupled to an end effector associated with the loading unit, the second pivoting member defining a second pivot axis that moves from a position aligned with the longitudinal axis to a position offset from the longitudinal axis when the first pivoting member is rotated; and
a movable interface between the first pivoting member and the second pivoting member.

11. A loading unit according to claim 10, further comprising a stationary gear coupled to a proximal end of the loading unit.

12. A loading unit according to claim 11, further comprising a movable gear coupling the second pivoting member to the end effector of the loading unit, wherein the movable gear is in operative engagement with the stationary gear and forms the movable interface.

13. A loading unit according to claim 12, wherein rotation of the first pivoting member in a clockwise direction, and the interaction between the stationary gear and the movable gear, causes rotation of the second pivoting member in the clockwise direction.

14. A loading unit according to claim 10, further comprising an articulation member coupled to the first pivoting member so that movement of the articulation member pivots the first pivoting member and the second pivoting member with respect to the longitudinal axis.

15. A loading unit according to claim 10, wherein the end effector includes a first jaw member and a second jaw member, the first jaw member and the second jaw member being movable from an open position wherein the jaw members are disposed in spaced relation relative to one another, to a clamping position wherein the jaw members are approximated relative to one another.

16. A loading unit according to claim 15, wherein the end effector includes a Staple cartridge assembly and an anvil assembly.

17. A surgical instrument comprising:
a housing;
an elongated portion extending distally from the housing and defining a longitudinal axis;
an end effector operably coupled to the elongated portion;
a first pivoting member pivotably coupled to a distal end of the elongated portion, the first pivoting member defining a first pivot axis intersecting the longitudinal axis;
a stationary gear coupled to the elongate portion, the first pivoting member being pivotable with respect to the stationary gear;
a second pivoting member pivotably coupled to the first pivoting member and coupled to the end effector, the second pivoting member defining a second pivot axis intersecting the longitudinal axis;
a movable gear coupled to the end effector and the second pivoting member; and
an articulation member coupled to the first pivoting member so that movement of the articulation member pivots the first pivoting member and the second pivoting member with respect to the longitudinal axis.

18. A surgical instrument according to claim 17, wherein the movable gear is in operative engagement with the stationary gear.

19. A surgical instrument according to claim 17, wherein at least one link operably couples the first pivoting member to the second pivoting member.

20. A surgical instrument according to claim 19, wherein the at least one link is pivotably connected to the elongated portion.

21. A surgical instrument according to claim 17, wherein the stationary gear is formed on a pivot plate coupled to the elongated portion.

22. A surgical instrument according to claim 21, wherein at least one link couples the first pivoting member to the second pivoting member, a proximal end of the at least one link being movable within an arcuate recess formed in the pivot plate.

23. A surgical instrument according to claim 17, wherein rotation of the proximal mounting assembly in a clockwise direction, and the interaction between the movable gear and the stationary gear, causes rotation of the second pivoting member in the clockwise direction.

24. A surgical instrument according to claim 17, wherein the end effector includes a first jaw member and a second jaw member, the first jaw member and the second jaw member being movable from an open position wherein the jaw members are disposed in spaced relation relative to one another, to a clamping position wherein the jaw members are approximated relative to one another.

25. A surgical instrument according to claim 24, wherein the end effector includes a staple cartridge assembly and an anvil assembly.

* * * * *